United States Patent [19]

Zones et al.

[11] Patent Number: 5,215,648

[45] Date of Patent: Jun. 1, 1993

[54] HYDROCARBON CONVERSION PROCESSES USING SSZ-31

[75] Inventors: Stacey I. Zones, San Francisco; Thomas V. Harris, Benicia; Andrew Rainis, Walnut Creek; Donald S. Santilli, Larkspur, all of Calif.

[73] Assignee: Chevron Research and Technology Company, San Francisco, Calif.

[21] Appl. No.: 817,260

[22] Filed: Jan. 3, 1992

Related U.S. Application Data

[60] Division of Ser. No. 471,158, Jan. 26, 1990, Pat. No. 5,106,801, which is a continuation-in-part of Ser. No. 260,439, Oct. 20, 1988, abandoned.

[51] Int. Cl.[5] .................. C10G 11/05; C07C 5/22

[52] U.S. Cl. .................. 208/46; 208/111; 208/120; 208/137; 585/418; 585/481; 585/640; 585/666; 585/739

[58] Field of Search .................. 208/46, 111, 138, 120; 585/418, 467, 481, 640

[56] References Cited

U.S. PATENT DOCUMENTS

| | | | |
|---|---|---|---|
| 5,007,997 | 4/1991 | Zones et al. | 208/46 |
| 5,087,347 | 2/1992 | Miller | 208/111 |
| 5,106,801 | 4/1992 | Zones et al. | 208/111 |

*Primary Examiner*—Anthony McFarlane
*Attorney, Agent, or Firm*—V. J. Cavalieri; C. E. Rincon

[57] ABSTRACT

Hydrocarbon conversion processes using a crystalline zeolite SSZ-31.

27 Claims, No Drawings

HYDROCARBON CONVERSION PROCESSES USING SSZ-31

CROSS-REFERENCE TO RELATED APPLICATIONS

This application is a division of application U.S. Ser. No. 471,158 filed Jan. 26, 1990, now U.S. Pat. No. 5,106,801, which is a continuation-in-part of U.S. Ser. No. 260,439 filed Oct. 20, 1988, now abandoned.

BACKGROUND OF THE INVENTION

Natural and synthetic zeolitic crystalline metalosilicates are useful as catalysts and adsorbents. Metalosilicate molecular sieves are zeolites with a silicate lattice wherein a metal can be substituted into the tetrahedral positions of the silicate framework. These metals include aluminum, gallium iron and mixtures thereof. These metalosilicates have distinct crystal structures which are demonstrated by X-ray diffraction. The crystal structure defines cavities and pores which are characteristic of the different species. The adsorptive and catalytic properties of each crystalline metalosilicate are determined in part by the dimensions of its pores and cavities. Thus, the utility of a particular zeolite in a particular application depends at least partly on its crystal structure.

Because of their unique molecular sieving characteristics, as well as their catalytic properties, some crystalline metalosilicates are especially useful in such applications as gas drying and separation and hydrocarbon conversion. Although many different crystalline aluminosilicates, borosilicate and silicates have been disclosed, there is a continuing need for new zeolites and silicates with desirable properties for gas separation and drying, hydrocarbon and chemical conversions, and other applications.

Crystalline aluminosilicates are usually prepared from aqueous reaction mixtures containing alkali or alkaline earth metal oxides, silica, and alumina. "Nitrogenous zeolites" have been prepared from reaction mixtures containing an organic templating agent, usually a nitrogen-containing organic cation. By varying the synthesis conditions and the composition of the reaction mixture, different zeolites can be formed using the same templating agent Use of N,N,N-trimethyl cyclopentylammonium iodide in the preparation of Zeolite SSZ-15 molecular sieve is disclosed in U.S. Pat. No. 4,610,854; use of 1-azoniaspiro [4.4] nonyl bromide and N,N,N-trimethyl neopentylammonium iodide in the preparation of a molecular sieve termed "Losod" is disclosed in Helv. Chim. Acta (1974); Vol. 57, p. 1533 (W. Sieber and W. M. Meier); use of quinuclidinium compounds to prepare a zeolite termed "NU-3" is disclosed in European Patent Publication No. 40016; use of 1,4-di(1-azoniabicyclo[2.2.2.]octane) lower alkyl compounds in the preparation of Zeolite SSZ-16 molecular sieve is disclosed in U.S. Pat. No. 4,508,837; use of N,N,N-trialkyl-1-adamantamine in the preparation of Zeolite SSZ-13 molecular sieve is disclosed in U.S. Pat. No. 4,544,538, and for SSZ-24 in U.S. Pat. No. 4,665,110.

Synthetic zeolitic crystalline borosilicates are useful as catalysts. Methods for preparing high silica content zeolites that contain framework boron are known and disclosed in U.S. Pat. No. 4,269,813. The amount of boron contained in the zeolite may be made to vary by incorporating different amounts of borate ion in the zeolite-forming solution. In some instances, it is necessary to provide boron as a pre-formed borosilicate.

The present invention relates to a novel family of stable synthetic crystalline materials identified as SSZ-31 and having a specified X-ray diffraction pattern, and also to the preparation and use of such materials.

SUMMARY OF THE INVENTION

We have prepared a family of crystalline metalosilicate molecular sieves with unique properties, referred to herein as "Zeolite SSZ-31" or simply "SSZ-31", and have found highly effective methods for preparing SSZ-31.

Metallosilicate molecular sieves are zeolites with a silicate lattice wherein a metal can be substituted into the tetrahedral positions of the silicate framework. These metals include aluminum, gallium, iron, boron, titanium and mixtures thereof.

The zeolite has compositions as synthesized and in the anhydrous state, in terms of oxides as follows: (1.0 to 5)$Q_2O$:(0.1 to 2.0)$M_2O$:$W'_2O_3$(greater than 50)$YO_2$, wherein M is an alkali metal cation, W is selected from boron, Y is selected from silicon, germanium and mixtures thereof, and Q is a cyclic quaternary ammonium ion; and (0.1 to 10)$Q'_2O$:(0.1 to 5.0)$M_2O$:$W'_2O_3$(greater than 100)$Y'O_2$, M is an alkali metal cation, W' is selected from aluminum, gallium, iron, and mixtures thereof, Y' is selected from silicon, germaninum and mixtures thereof and Q, is a tricyclodecane quarternary ammonium ion.

SSZ-31 zeolites may be prepared using various methods. The method for preparing SSZ-31 with a $YO_2$:$W_2O_3$ mole ratio greater than 50:1 comprises preparing an aqueous mixture containing sources of a quaternary ammonium ion, an alkali oxide, an oxide selected from boron as a borosilicate, not simply a boron oxide, and an oxide selected from silicon oxide, germanium oxide, and mixtures thereof, and having a composition, in terms of mole ratios of oxides, falling within the following ranges: $YO_2$/$W_2O_3$, greater than 50:1; wherein Y is selected from silicon, germanium, and mixtures thereof, W is selected from boron, and Q is a quaternary ammonium ion; maintaining the mixture at a temperature of at least 100° C. until the crystals of said zeolite are formed; and recovering said crystals.

A preferred borosilicate source is boron beta zeolite described in commonly assigned co-pending application U.S. Ser. No. 377,359 filed Jul. 7, 1989, and entitled "Low-Aluminum Boron Beta Zeolite".

The method for preparing SSZ-31 with a $Y'O_2$:$W'_2O_3$ mole ratio greater than 100:1 comprises preparing an aqueous mixture containing sources of a tricyclodecane quaternary ammonium ion, an oxide selected from aluminum oxide, gallium oxide, iron oxide, and mixtures thereof, and an oxide selected from silicon oxide, germanium oxide, and mixtures thereof, and having a composition, in terms of mole ratios of oxides, falling within the following ranges: $Y'O_2$/$W'_2O_3$, 100:1 to infinity (essentially pure $Y'O_2$); wherein Y' is selected from silicon, germanium, and mixtures thereof, W' is selected from aluminum, gallium, iron, and mixtures thereof, and Q' is a tricyclodecane quaternary ammonium ion; maintaining the mixture at a temperature of at least 100° C. until the crystals of said zeolite are formed; and recovering said crystals.

We have found that the SSZ-31 zeolite has unexpectedly outstanding hydrocarbon conversion properties, particularly including hydrocracking, chemicals production, reforming and catalytic cracking.

DETAILED DESCRIPTION OF THE INVENTION

SSZ-31 zeolites, as synthesized, have a crystalline structure whose X-ray powder diffraction pattern shows the following characteristic lines:

TABLE 1

| $2\theta$ | d/n | $I/I_o$ |
|---|---|---|
| 6.10 | 14.49 | 6 |
| 7.38 | 11.98 | 30 |
| 8.18 | 10.81 | 11 |
| 20.30 | 4.37 | 15 |
| 21.12 | 4.21 | 69 |
| 22.25 | 3.99 | 100 |
| 24.73 | 3.60 | 23 |
| 30.90 | 2.89 | 11 |

Typical SSZ-31 borosilicate zeolites have the X-ray diffraction patterns of Table 6 below.

As demonstrated in Tables 1 and 6, the position of the X-ray diffraction pattern lines will stay the same after removal of the organic template, but the relative intensity of these lines will change.

X-ray powder diffraction patterns were determined by standard techniques. The radiation was the K-alpha/doublet of copper and a scintillation counter spectrometer with a strip chart pen recorder was used. The peak heights I and the positions, as a function of $2\theta$ where $\theta$ is the Bragg angle, were read from the spectrometer chart. From these measured values, the relative intensities, $100I/I_o$, where $I_o$ is the intensity of the strongest line or peak, and d, the interplanar spacing in Angstroms corresponding to the recorded lines, can be calculated. The X-ray diffraction pattern of Table 1 is characteristic of SSZ-31 zeolites. The zeolite produced by exchanging the metal or other cations present in the zeolite with various other cations yields substantially the same diffraction pattern although there can be minor shifts in interplanar spacing and minor variations in relative intensity. Minor variations in the diffraction pattern can also result from variations in the organic compound used in the preparation and from variations in the silica-to-alumina mole ratio from sample to sample. Calcination can also cause minor shifts in the X-ray diffraction pattern. Notwithstanding these minor perturbations, the basic crystal lattice structure remains unchanged.

Various methods can be used to prepare the SSZ-31 zeolite. SSZ-31 zeolites with a $YO_2:W_2O_3$ mole ratio greater than 50:1 can be suitably prepared from an aqueous solution containing sources of an alkali metal oxide, a quaternary ammonium ion, borosilicate, and an oxide of silicon or germanium, or mixture of the two. The reaction mixture should have a composition in terms of mole ratios falling within the following ranges:

|  | Broad | Preferred |
|---|---|---|
| $YO_2/W_2O_3$ | 30–∞ | 50–∞ |
| $OH/YO_2$ | 0.10–0.50 | 0.15–0.25 |
| $Q/YO_2$ | 0.05–0.50 | 0.10–0.25 |
| $M+/YO_2$ | 0.05–0.30 | 0.05–0.15 |
| $H_2O/YO_2$ | 15–300 | 25–60 |
| $Q/Q+M+$ | 0.30–0.70 | 0.40–0.60 |

|  | Broad | Preferred |
|---|---|---|
| $YO_2/W_2O_3$ | 30–∞ | 50–∞ |
| $OH/YO_2$ | 0.10–0.50 | 0.15–0.25 |
| $Q/YO_2$ | 0.05–0.50 | 0.10–0.25 |
| $M+/YO_2$ | 0.05–0.30 | 0.05–0.15 |
| $H_2O/YO_2$ | 15–300 | 25–60 |
| $Q/Q+M+$ | 0.30–0.70 | 0.40–0.60 | wherein Q is a quaternary ammonium ion, Y is silicon, germanium or both, and W is boron. M is an alkali metal, preferably sodium. The organic compound which acts as a source of the quaternary ammonium ion employed can provide hydroxide ion. W is shown as boron, but is provided to the reaction as borosilicate. The quaternary ammonium compounds which may be used to prepare these SSZ-31 zeolites are shown in Table 2 as Templates B–F. Examples 12, 13, 14, 15 and 16 sow methods as preparing the Templates B–F in Table 2.

When using the quaternary ammonium hydroxide compound as a template, it has also been found that purer forms of SSZ-31 are prepared when there is an excess of compound present relative to the amount of alkali metal hydroxide.

TABLE 2

Organo-Cations Which Are Representative of Directing Boron SSZ-31 Synthesis

| Structure | Template |
|---|---|
| 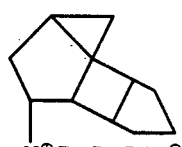 $N^{\oplus}(R_1, R_2, R_3)A^{\ominus}$ N,N,N trimethylammonium-8-tricyclo[5.2.1.0]decane | A |
| 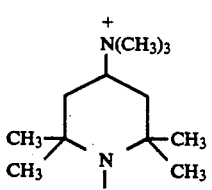 4 trimethylammonium-2,2,6,6 tetramethy piperidine | B |
| 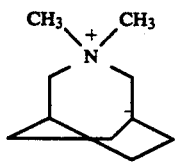 N,N dimethyl-3-azonium bicyclo[3.2.2]nonane | C |
| 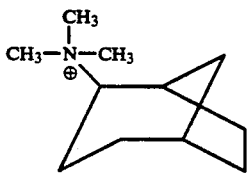 N,N,N trimethylammonium-2-bicyclo[3.2.1]octane | D |

TABLE 2-continued
Organo-Cations Which Are Representative of Directing Boron SSZ-31 Synthesis

| Structure | Template |
|---|---|
| 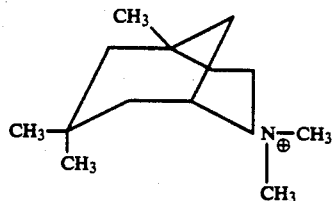 N,N dimethyl-6-azonium,1,3,3-trimethyl-bicyclo [3.2.1]octane | E |
| 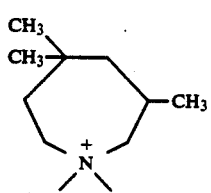 N,N,3,5,5,pentamethyl azonium cycloheptane | F |

The reaction mixture is prepared using standard zeolitic preparation techniques. Sources of borosilicates for the reaction mixture include borosilicate glasses and most particularly, other reactive borosilicate molecular sieves. One very reactive source is boron beta zeolite described in commonly assigned co-pending application U.S. Ser. No. 377,359, filed Jul. 7, 1989, and entitled "Low-Aluminum Boron Beta Zeolite". Typical sources of silicon oxide include silicates, silica hydrogel, silicic acid, colloidal silica, fumed silica, tetra-alkyl orthosilicates, and silica hydroxides.

The reaction mixture is maintained at an elevated temperature until the crystals of the zeolite are formed. The temperatures during the hydrothermal crystallization step are typically maintained from about 120° C. to about 200° C., preferably from about 130° C. to about 170° C. and most preferably from about 135° C. to about 165° C. The crystallization period is typically greater than one day and preferably from about three days to about seven days.

The hydrothermal crystallization is conducted under pressure and usually in an autoclave so that the reaction mixture is subject to autogenous pressure. The reaction mixture can be stirred during crystallization.

Once the zeolite crystals have formed, the solid product is separated from the reaction mixture by standard mechanical separation techniques such as filtration. The crystals are water-washed and then dried, e.g., at 90° C. to 150° C. from 8 to 24 hours, to obtain the as synthesized, SSZ-31 zeolite crystals. The drying step can be performed at atmospheric or subatmospheric pressures.

During the hydrothermal crystallization step, the SSZ-31 crystals can be allowed to nucleate spontaneously from the reaction mixture. The reaction mixture can also be seeded with SSZ-31 crystals both to direct and accelerate the crystallization, as well as to minimize the formation of undesired borosilicate contaminants.

SSZ-31 with a Y'O$_2$:W'$_2$O$_3$ mole ratio greater than 100:1 can be suitably prepared from an aqueous solution containing sources of an alkali metal oxide, a tricyclodecane quaternary ammonium ion, an oxide of aluminum, gallium, iron, or mixtures thereof, and an oxide of silicon or germanium, or mixture of the two. The reaction mixture should have a composition in terms of mole ratios falling within the following ranges:

| | Broad | Preferred |
|---|---|---|
| Y'O$_2$/W'$_2$O$_3$ | 100–∞ | 200–∞ |
| OH$^-$/Y'O$_2$ | 0.10–0.60 | 0.20–0.50 |
| Q'/Y'O$_2$ | 0.05–0.50 | 0.10–0.40 |
| M$^+$/Y'O$_2$ | 0.05–0.30 | 0.05–0.15 |
| H$_2$O/Y'O$_2$ | 10–300 | 25–60 |
| Q'/Q'+M$^+$ | 0.30–0.80 | 0.40–0.75 | wherein Q' is a tricyclodecane quaternary ammonium ion, Y' is silicon, germanium or both, and W' is aluminum, gallium, iron, or mixtures thereof. M is an alkali metal, preferably sodium or potassium. The organic tricyclodecane compound which acts as a source of the quaternary ammonium ion employed can provide hydroxide ion.

When using the quaternary ammonium hydroxide compound as a template, it has also been found that purer forms of SSZ-31 are prepared when there is an excess of tricyclodecane compound present relative to the amount of alkali metal hydroxide and that when the OH$^-$/SiO$_2$ molar ratio is greater than 0.40, then M$^+$/SiO$_2$ molar ratio should be less than 0.20.

The quaternary ammonium ion component Q, of the crystallization mixture, is derived from a [5.2.1.0] tricyclodecane quaternary ammonium compound with the nitrogen at the eight position of the ring system. Preferably, the quaternary ammonium ion is derived from a compound of the Formula (1):

(1)

N$^\oplus$(R$_1$, R$_2$, R$_3$)A$^\ominus$ wherein each of R$_1$, R$_2$ and R$_3$ independently is lower alkyl and most preferably methyl; and A$^\theta$ is an anion which is not detrimental to the formation of the zeolite. A method of making this template is described in Example 1.

The tricyclodecane quaternary ammonium compounds of the Formula (1) above are prepared by methods known in the art. For example, compounds of the Formula (1) wherein A$^\theta$ is a halide may be prepared by reacting an N,N-di(lower)alkyl-8-amino tricyclo [5.2.1.0] decane compound of the Formula (2):

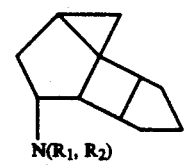

(2)

N(R$_1$, R$_2$)

wherein each of R$_1$ and R$_2$ independently is lower alkyl, with a lower alkyl halide, in a solvent such as ethyl acetate. The halide anion may be ion exchanged to obtain other anions such as hydroxide, acetate, sulfate, carboxydate, and the like The N,N-di(lower)alkyl-8-amino tricycle [5.2.1.0] decane of the Formula (2) above may be prepared by reacting 8-ketotricyclo [5.2.1.0] decane with a lower dialkyl formamide in the presence of formic acid at a temperature in the range of 160°–195° C. in a closed system. The reaction can be carried out for 10–50 hours, with the product recovered by partitioning between ether and a basic aqueous solution.

By "lower alkyl" is meant alkyl of from about 1 to 3 carbon atoms.

$A^\theta$ is an anion which is not detrimental to the formation of the zeolite. Representative of the anions include halogen, e.g., fluoride, chloride, bromide and iodide, hydroxide, acetate, sulfate, carboxylate, etc. Hydroxide is the most preferred anion. It may be beneficial to ion-exchange, for example, the halide for hydroxide ion, thereby reducing or eliminating the alkali metal hydroxide quantity required.

The reaction mixture is prepared using standard zeolitic preparation techniques. Typical sources of aluminum oxide for the reaction mixture include aluminates, alumina, other zeolites, and aluminum compounds such as $AlCl_3$ and $Al_2(SO_4)_3$, and colloidal dispersions of alumina and alumina on silica, such as the Nalco product 1SJ612. Typical sources of silicon oxide include silicates, silica hydrogel, silicic acid, colloidal silica, tetraalkyl orthosilicates, and silica hydroxides. Gallium, iron, and germanium can be added in forms corresponding to their aluminum and silicon counterparts. Salts, particularly alkali metal halides such as sodium chloride, can be added to or formed in the reaction mixture. They are disclosed in the literature as aiding the crystallization of zeolites while preventing silica occlusion in the lattice.

The reaction mixture is maintained at an elevated temperature until the crystals of the zeolite are formed. The temperatures during the hydrothermal crystallization step are typically maintained from about 140° C. to about 200° C., preferably from about 150° C. to about 170° C., and most preferably from about 155° C. to about 165° C. The crystallization period is typically greater than 1 day and preferably from about 6 days to about 12 days.

The hydrothermal crystallization is conducted under pressure and usually in an autoclave so that the reaction mixture is subject to autogenous pressure. The reaction mixture can be stirred during crystallization.

Once the zeolite crystals have formed, the solid product is separated from the reaction mixture by standard mechanical separation techniques such as filtration. The crystals are water-washed and then dried, e.g., at 90° C. to 150° C. for from 8 to 24 hours, to obtain the as synthesized, SSZ-31 zeolite crystals The drying step can be performed at atmospheric or subatmospheric pressures.

During the hydrothermal crystallization step, the SSZ-31 crystals can be allowed to nucleate spontaneously from the reaction mixture. The reaction mixture can also be seeded with SSZ-31 crystals both to direct, and accelerate the crystallization, as well as to minimize the formation of undesired aluminosilicate contaminants.

The synthetic SSZ-31 zeolites can be used as synthesized or can be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica:alumina mole ratio. The zeolite can also be steamed; steaming helps stabilize the crystalline lattice to attack from acids. The zeolite can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired. Typical replacing cations can include metal cations, e.g., rare earth, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, Fe, and Co are particularly preferred.

The hydrogen, ammonium, and metal components can be exchanged into the zeolite. The zeolite can also be impregnated with the metals, or, the metals can be physically intimately admixed with the zeolite using standard methods known to the art. And, some metals can be occluded in the crystal lattice by having the desired metals present as ions in the reaction mixture from which the SSZ-31 zeolite is prepared.

Typical ion exchange techniques involve contacting the synthetic zeolite with a solution containing a salt of the desired replacing cation or cations. Although a wide variety of salts can be employed, chlorides and other halides, nitrates, and sulfates are particularly preferred. Representative ion exchange techniques are disclosed in a wide variety of patents including U.S. Pat. Nos. 3,140,249; 3,140,251; and 3,140,253. Ion exchange can take place either before or after the zeolite is calcined.

Following contact with the salt solution of the desired replacing cation, the zeolite is typically washed with water and dried at temperatures ranging from 65° C. to about 315° C. After washing, the zeolite can be calcined in air or inert gas at temperatures ranging from about 200° C. to 820° C. for periods of time ranging from 1 to 48 hours, or more, to produce a catalytically active product especially useful in hydrocarbon conversion processes.

Regardless of the cations present in the synthesized form of the zeolite, the spatial arrangement of the atoms which form the basic crystal lattice of the zeolite remains essentially unchanged. The exchange of cations has little, if any, effect on the zeolite lattice structures.

The SSZ-31 zeolites can be formed into a wide variety of physical shapes. Generally speaking, the zeolite can be in the form of a powder, a granule, or a molded product, such as extrudate having particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or, dried or partially dried and then extruded. The zeolite can be composited with other materials resistant to the temperatures and other conditions employed in organic conversion processes. Such matrix materials include active and inactive materials and synthetic or naturally occurring zeolites as well as inorganic materials such as clays, silica and metal oxides. The latter may occur naturally or may be in the form of gelatinous precipitates, sols, or gels, including mixtures of silica and metal oxides. Use of an active material in conjunction with the synthetic zeolite, i.e., combined with it, tends to improve the conversion and selectivity of the catalyst in certain organic conversion processes. Inactive materials can suitably serve as diluents to control the amount of conversion in a given process so that products can be obtained economically without using other means for controlling the rate of reaction. Frequently, zeolite materials have been incorporated into naturally occurring clays, e.g., bentonite and kaolin.

These materials, i.e., clays, oxides, etc., function, in part, as binders for the catalyst It is desirable to provide a catalyst having good crush strength, because in petroleum refining the catalyst is often subjected to rough handling. This tends to break the catalyst down into powders which cause problems in processing.

Naturally occurring clays which can be composited with the synthetic zeolites of this invention include the montmorillonite and kaolin families, which families include the sub-bentonites and the kaolins commonly known as Dixie, McNamee, Ga., and Florida clays or others in which the main mineral constituent is halloysite, kaolinite, dickite, nacrite, or anauxite. Fibrous clays such as sepiolite and attapulgite can also be used as supports. Such clays can be used in the raw state as originally mined or can be initially subjected to calcination, acid treatment or chemical modification.

In addition to the foregoing materials, the SSZ-31 zeolites can be composited with porous matrix materials and mixtures of matrix materials such as silica, alumina, titania, magnesia, silica:alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia, and silica-magnesia-zirconia. The matrix can be in the form of a cogel.

The SSZ-31 zeolites can also be composited with other zeolites such as synthetic and natural faujasites (e.g., X and Y), erionites, and mordenites. They can also be composited with purely synthetic zeolites such as those of the ZSM series. The combination of zeolites can also be composited in a porous inorganic matrix.

SSZ-31 zeolites are useful in hydrocarbon conversion reactions. Hydrocarbon conversion reactions are chemical and catalytic processes in which carbon-containing compounds are changed to different carbon-containing compounds. Examples of hydrocarbon conversion reactions include catalytic cracking, hydrocracking, and olefin and aromatics formation reactions. The catalysts are useful in other petroleum refining and hydrocarbon conversion reactions such as isomerizing n-paraffins and naphthenes, polymerizing and oligomerizing olefinic or acetylenic compounds such as isobutylene and butene-1, reforming, alkylating, isomerizing polyalkyl substituted aromatics (e.g., ortho xylene), and disproportionating aromatics (e.g., toluene) to provide mixtures of benzene, xylenes, and higher methylbenzenes. The SSZ-31 catalysts have high selectivity, and under hydrocarbon conversion conditions can provide a high percentage of desired products relative to total products.

SSZ-31 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, and in general, can be any carbon containing fluid susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that processing will generally be more efficient (and the catalyst more active) if the metal, nitrogen, and sulfur content of the feedstock is lower.

Using the SSZ-31 catalyst which contains aluminum framework substitution and a hydrogenation promoter, heavy petroleum residual feedstocks, cyclic stocks, and other hydrocracking charge stocks can be hydrocracked at hydrocracking conditions including a temperature in the range of from 175° C. to 485° C., molar ratios of hydrogen to hydrocarbon charge from 1 to 100, a pressure in the range of from 0.5 to 350 bar, and a liquid hourly space velocity (LHSV) in the range of from 0.1 to 30.

Hydrocracking catalysts comprising SSZ-31 contain an effective amount of at least one hydrogenation catalyst (component) of the type commonly employed in hydrocracking catalysts. The hydrogenation component is generally selected from the group of hydrogenation catalysts consisting of one or more metals of Group VIB and Group VIII, including the salts, complexes, and solutions containing such. The hydrogenation catalyst is preferably selected from the group of metals, salts, and complexes thereof of the group consisting of at least one of platinum, palladium, rhodium, iridium, and mixtures thereof or the group consisting of at least one of nickel, molybdenum, cobalt, tungsten, titanium, chromium, and mixtures thereof. Reference to the catalytically active metal or metals is intended to encompass such metal or metals in the elemental state or in some form such as an oxide, sulfide, halide, carboxylate, and the like.

A hydrogenation component is present in the hydrocracking catalyst in an effective amount to provide the hydrogenation function of the hydrocracking catalyst and preferably in the range of from 0.05% to 25% by weight.

SSZ-31 may be used to dewax a variety of feedstocks ranging from relatively light distillate fractions up to high boiling stocks such as whole crude petroleum, reduced crudes, vacuum tower residua, cycle oils, synthetic crudes (e.g., shale oils, tar sand oil, etc.), gas oils, vacuum gas oils, foots oils, and other heavy oils. The feedstock will normally be a $C_{10}+$ feedstock generally boiling above about 350° F. since lighter oils will usually be free of significant quantities of waxy components. However, the process is particularly useful with waxy distillate stocks such as middle distillate stocks including gas oils, kerosenes, and jet fuels, lubricating oil stocks, heating oils and other distillate fractions whose pour point and viscosity need to be maintained within certain specification limits.

Lubricating oil stocks will generally boil above 230° C. (450° F.), more usually above 315° C. (600° F.). Hydrocracked stocks are a convenient source of lubricating stocks of this kind and also of other distillate fractions since they normally contain significant amounts of waxy n-paraffins. The feedstock of the present process will normally be a $C_{10}+$ feedstock containing paraffins, olefins, naphthenes, aromatics and heterocyclic compounds and with a substantial proportion of higher molecular weight n-paraffins and slightly branched paraffins which contribute to the waxy nature of the feedstock.

The catalytic dewaxing conditions are dependent in large measure on the feed used and upon the desired pour point. Generally, the temperature will be between about 200° C. and about 475° C., preferably between about 250° C. and about 450° C. The pressure is typically between about 15 psig and about 3000 psig, preferably between about 200 psig and 3000 psig. The liquid hourly space velocity (LHSV) preferably will be from 0.1 to 20, preferably between about 0.2 and about 10.

Hydrogen is preferably present in the reaction zone during the catalytic dewaxing process. The hydrogen to feed ratio is typically between about 500 and about 30,000 SCF/bbl (standard cubic feet per barrel), preferably about 1,000 to about 20,000 SCF/bbl. Generally, hydrogen will be separated from the product and recycled to the reaction zone. Typical feedstocks include light gas-oil, heavy gas-oils, and reduced crudes boiling about 350° F.

The SSZ-31 hydrodewaxing catalyst may optionally contain a hydrogenation component of the type commonly employed in dewaxing catalysts. The hydrogenation component may be selected from the group of hydrogenation catalysts consisting of one or more metals of Group VIB and Group VIII, including the salts, complexes and solutions containing such metals. The preferred hydrogenation catalyst is at least one of the group of metals, salts, and complexes selected from the group consisting of at least one of platinum, palladium, rhodium, iridium, and mixtures thereof or at least one from the group consisting of nickel, molybdenum, cobalt, tungsten, titanium, chromium, and mixtures thereof. Reference to the catalytically active metal or metals is intended to encompass such metal or metals in the elemental state or in some form such as an oxide, sulfide, halide, carboxylate, and the like.

The hydrogenation component of the hydrodewaxing catalyst is present in an effective amount to provide an effective hydrodewaxing catalyst preferably in the range of from about 0.05 to 5% by weight.

The SSZ-31 hydrodewaxing catalyst may be used alone or in conjunction with intermediate-pore (or medium-pore) molecular sieves. These intermediate-pore molecular sieves are shape selective in that they have a pore size which admits straight-chain n-paraffins either alone or with only slightly branched-chain paraffins but which exclude more highly branched materials and cycloaliphatics. Molecular sieves such as ZSM-5, ZSM-11, ZSM-12, ZSM-22, ZSM-23 and SAPO-11 are suitable for this purpose.

The intermediate-pore molecular sieves may be combined with the SSZ-31 or the isomerization dewaxing step using SSZ-31 may be followed by a separate selective dewaxing step using the intermediate-pore molecular sieves.

The relative amounts of the SSZ-31 component and shape selective intermediate-pore molecular sieve component, if any, will depend at least in part, on the selected hydrocarbon feedstock and on the desired product distribution to be obtained therefrom, but in all instances an effective amount of SSZ-31 is employed. When a shape selective molecular sieve component is employed, the relative weight ratio of the shape selective molecular sieve to the SSZ-31 is generally between about 10:1 and about 1:500, desirably between about 10:1 and about 1:200, preferably between about 2:1 and about 1:50, and most preferably is between about 1:1 and about 1:20.

SSZ-31 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial aromatics content by contacting the hydrocarbon feed with the zeolite at a temperature in the range of from about 400° C. to 600° C., preferably 480° C. to 550° C. at pressures ranging from atmospheric to 10 bar, and LHSV ranging from 0.1 to 15.

The conversion catalyst preferably contain a Group VIII metal compound to have sufficient activity for commercial use By Group VIII metal compound as used herein is meant the metal itself or a compound thereof. The Group VIII noble metals and their compounds, platinum, palladium, and iridium, or combinations thereof can be used. The most preferred metal is platinum. The amount of Group VIII metal present in the conversion catalyst should be within the normal range of use in reforming catalysts, from about 0.05 to 2.0 wt. %, preferably 0.2 to 0.8 wt. %.

The zeolite/Group VIII metal conversion catalyst can be used without a binder or matrix. The preferred inorganic matrix, where one is used, is a silica-based binder such as Cab-O-Sil or Ludox. Other matrices such as magnesia and titania can be used. The preferred inorganic matrix is nonacidic.

It is critical to the selective production of aromatics in useful quantities that the conversion catalyst be substantially free of acidity, for example, by poisoning the zeolite with a basic metal, e.g., alkali metal, compound. The zeolite is usually prepared from mixtures containing alkali metal hydroxides and thus, have alkali metal contents of about 1–2 wt. %. These high levels of alkali metal, usually sodium or potassium, are unacceptable for most catalytic applications because they greatly deactivate the catalyst for cracking reactions. Usually, the alkali metal is removed to low levels by ion exchange with hydrogen or ammonium ions. By alkali metal compound as used herein is meant elemental or ionic alkali metals or their basic compounds. Surprisingly, unless the zeolite itself is substantially free of acidity, the basic compound is required in the present process to direct the synthetic reactions to aromatics production.

The amount of alkali metal necessary to render the zeolite substantially free of acidity can be calculated using standard techniques based on the aluminum, gallium or iron content of the zeolite. If a zeolite free of alkali metal is the starting material, alkali metal ions can be ion exchanged into the zeolite to substantially eliminate the acidity of the zeolite. An alkali metal content of about 100%, or greater, of the acid sites calculated on a molar basis is sufficient.

Where the basic metal content is less than 100% of the acid sites on a molar basis, the test described in U.S. Pat. No. 4,347,394 which patent is incorporated herein by reference, can be used to determine if the zeolite is substantially free of acidity.

The preferred alkali metals are sodium, potassium, and cesium. The zeolite itself can be substantially free of acidity only at very high silica:alumina mole ratios; by "zeolite consisting essentially of silica" is meant a zeolite which is substantially free of acidity without base poisoning.

Hydrocarbon cracking stocks can be catalytically cracked in the absence of hydrogen using SSZ-31 at LHSV from 0.5 to 50, temperatures from about 260° F. to 1625° F. and pressures from subatmospheric to several hundred atmospheres, typically from about atmospheric to about five atmospheres.

For this purpose, the SSZ-31 catalyst can be composited with mixtures of inorganic oxide supports as well as traditional cracking catalyst.

The catalyst may be employed in conjunction with traditional cracking catalysts, e.g., any aluminosilicate heretofore employed as a component in cracking catalysts. Representative of the zeolitic aluminosilicates disclosed heretofore as employable as component parts of cracking catalysts are Zeolite Y (including steam stabilized chemically modified, e.g., ultra-stable Y), Zeolite X, Zeolite beta (U.S. Pat. No. 3,308,069), Zeolite ZK-20 (U.S. Pat. No. 3,445,727), Zeolite ZSM-3 (U.S. Pat. No. 3,415,736), faujasite, LZ-10 (U.K. Patent 2,014,970, Jun. 9, 1982), ZSM-5-Type Zeolites, e.g., ZSM-5, ZSM-11, ZSM-12, ZSM-23, ZSM-35, ZSM-38, ZSM-48, crystalline silicates such as silicalite (U.S. Pat. No. 4,061,724), erionite, mordenite, offretite, chabazite, FU-1-type zeolite, NU-type zeolites, LZ-210-type zeolite and mixtures thereof. Traditional cracking catalysts containing amounts of $Na_2O$ less than about one percent by weight are generally preferred. The relative amounts of the SSZ-31 component and traditional cracking component, if any, will depend at least in part, on the selected hydrocarbon feedstock and on the desired product distribution to be obtained therefrom, but in all instances, an effective amount of SSZ-31 is employed. When a traditional cracking catalyst (TC) component is employed, the relative weight ratio of the TC to the SSZ-31 is generally between about 1:10 and about 500:1, desirably between about 1:10 and about 200:1, preferably between about 1:2 and about 50:1, and most preferably between about 1:1 and about 20:1.

The cracking catalysts are typically employed with an inorganic oxide matrix component which may be any of the inorganic oxide matrix components which have been employed heretofore in the formulation of FCC catalysts including: amorphous catalytic inorganic oxides, e.g., catalytically active silica-aluminas, clays, silicas, aluminas, silica-aluminas, silica-zirconias, silica-magnesias, alumina-borias, alumina-titanias, and the like and mixtures thereof. The traditional cracking component and SSZ-31 may be mixed separately with the matrix component and then mixed or the TC component and SSZ-31 may be mixed and then formed with the matrix component.

The mixture of a traditional cracking catalyst and SSZ-31 may be carried out in any manner which results in the coincident presence of such in contact with the crude oil feedstock under catalytic cracking conditions. For example, a catalyst may be employed containing the traditional cracking catalyst and a SSZ-31 in single catalyst particles or SSZ-31 with or without a matrix component may be added as a discrete component to a traditional cracking catalyst.

SSZ-31 can also be used to oligomerize straight and branched chain olefins having from about 2-21 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous state phase with SSZ-31 at a temperature of from about 450° F. to about 1200° F., a WHSV of from about 0.2 to about 50 and a hydrocarbon partial pressure of from about 0.1 to about 50 atmospheres.

Also, temperatures below about 450° F. may be used to oligomerize the feedstock, when the feedstock is in the liquid phase when contacting the zeolite catalyst. Thus, when the olefin feedstock contacts the zeolite catalyst in the liquid phase, temperatures of from about 50° F. to about 450° F., and preferably from 80° to 400° F. may be used and a WHSV of from about 0.05 to 20 and preferably 0.1 to 10. It will be appreciated that the pressures employed must be sufficient to maintain the system in the liquid phase. As is known in the art, the pressure will be a function of the number of carbon atoms of the feed olefin and the temperature. Suitable pressures include from about 0 psig to about 3000 psig.

The zeolite can have the original cations associated therewith replaced by a wide variety of other cations according to techniques well known in the art. Typical cations would include hydrogen, ammonium, and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the zeolite have a fairly low aromatization activity, i.e., in which the amount of aromatics produced is not more than about 20 wt. %. This is accomplished by using a zeolite with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 which is incorporated herein by reference. If required, such zeolites may be obtained by steaming, by use in a conversion process or by any other method which may occur to one skilled in this art.

SSZ-31 can be used to convert light gas $C_2$–$C_6$ paraffins and/or olefins to higher molecular weight hydrocarbons including aromatic compounds. Operating temperatures of 100°–700° C., operating pressures of 0–1000 psig and space velocities of 0.5–40 hr$^{-1}$ WHSV can be used to convert the $C_2$–$C_6$ paraffin and/or olefins to aromatic compounds. Preferably, the zeolite will contain a catalyst metal or metal oxide wherein said metal is selected from the group consisting of Group IB, IIB, IIIA, or VIII of the Periodic Table, and most preferably, gallium or zinc and in the range of from about 0.05–5 wt. %.

SSZ-31 can be used to condense lower aliphatic alcohols having 1–10 carbon atoms to a gasoline boiling point hydrocarbon product comprising mixed aliphatic and aromatic hydrocarbons. Preferred condensation reaction condition using SSZ-31 as the condensation catalyst include a temperature of about 500°–1000° F., a pressure of about 0.5–1000 psig and a space velocity of about 0.5–50 WHSV. U.S. Pat. No. 3,984,107 describes the condensation process conditions in more detail. The disclosure of U.S. Pat. No. 3,984,107 is incorporated herein by reference.

The SSZ-31 catalyst may be in the hydrogen form or may be base exchanged or impregnated to contain ammonium or a metal cation complement, preferably in the range of from about 0.05–5 wt. %. The metal cations that may be present include any of the metals of the Groups I-VIII of the Periodic Table. However, in the case of Group IA metals, the cation content should in no case be so large as to effectively inactivate the catalyst.

The present SSZ-31 catalyst is highly active and highly selective for isomerizing $C_4$ to $C_7$ hydrocarbons. The activity means that the catalyst can operate at relatively low temperatures which thermodynamically favors highly branched paraffins. Consequently, the catalyst can produce a high octane product. The high selectivity means that a relatively high liquid yield can be achieved when the catalyst is run at a high octane.

The isomerization process comprises contacting the isomerization catalyst with a hydrocarbon feed under isomerization conditions. The feed is preferably a light straight run fraction, boiling within the range of 30°–250° F. and preferably from 60°–200° F. Preferably, the hydrocarbon feed for the process comprises a substantial amount of $C_4$ to $C_7$ normal and slightly branched low octane hydrocarbons, more preferably $C_5$ and $C_6$ hydrocarbons.

The pressure in the process is preferably between 50 psig, more preferably between 100–500 psig. The LHSV is preferably between about 1 to about 10 with a value in the range of about 1 to about 4 being more preferred. It is also preferable to carry out the isomerization reaction in the presence of hydrogen. Preferably, hydrogen is added to give a hydrogen to hydrocarbon ratio ($H_2/HC$) of between 0.5 and 10 $H_2/HC$, more preferably between 1 and 8 $H_2/HC$. The temperature is preferably between about 200° F. and about 1000° F., more preferably between 400°–600° F. As is well known to those skilled in the isomerization art, the initial selection of the temperature within this broad range is made primarily as a function of the desired conversion level considering the characteristics of the feed and of the catalyst. Thereafter, to provide a relatively constant value for conversion, the temperature may have to be slowly increased during the run to compensate for any deactivation that occurs.

A low sulfur feed is especially preferred in the isomerization process. The feed preferably contains less than 10 ppm, more preferably less than 1 ppm, and most preferably less than 0.1 ppm sulfur. In the case of a feed which is not already low in sulfur, acceptable levels can be reached by hydrogenating the feed in a presaturation zone with a hydrogenating catalyst which is resistant to sulfur poisoning. An example of a suitable catalyst for this hydrodesulfurization process is an alumina-containing support and a minor catalytic proportion of molybdenum oxide, cobalt oxide and/or nickel oxide. A platinum on alumina hydrogenating catalyst can also work. In which case, a sulfur sorber is preferably placed downstream of the hydrogenating catalyst, but upstream of the present isomerization catalyst. Examples of sulfur sorbers are alkali or alkaline earth metals on porous refractory inorganic oxides, zinc, etc. Hydrodesulfurization is typically conducted at 315°–455° C., at 200–2000 psig, and at a LHSV of 1–5.

It is preferable to limit the nitrogen level and the water content of the feed. Catalysts and processes which are suitable for these purposes are known to those skilled in the art.

After a period of operation, the catalyst can become deactivated by sulfur or coke. Sulfur and coke can be removed by contacting the catalyst with an oxygen-containing gas at an elevated temperature. If the Group VIII metal(s) has agglomerated, then it can be redispersed by contacting the catalyst with a chlorine gas under conditions effective to redisperse the metal(s). The method of regenerating the catalyst may depend on whether there is a fixed bed, moving bed, or fluidized bed operation. Regeneration methods and conditions are well known in the art.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium and tin may also be used in conjunction with the noble metal. The most preferred metal is platinum. The amount of Group VIII metal present in the conversion catalyst should be within the normal range of use in isomerizing catalysts, from about 0.05–2.0 wt. %.

SSZ-31 can be used in a process for the alkylation or transalkylation of an aromatic hydrocarbon. The process comprises contacting the aromatic hydrocarbon with a $C_2$ to $C_4$ olefin alkylating agent or a polyalkyl aromatic hydrocarbon transalkylating agent, under at least partial liquid phase conditions, and in the presence of a catalyst comprising SSZ-31.

For high catalytic activity, the SSZ-31 zeolite should be predominantly in its hydrogen ion form. Generally, the zeolite is converted to its hydrogen form by ammonium exchange followed by calcination. If the zeolite is synthesized with a high enough ratio of organo-nitrogen cation to sodium ion, calcination alone may be sufficient. It is preferred that, after calcination, at least 80% of the cation sites are occupied by hydrogen ions and/or rare earth ions.

The pure SSZ-31 zeolite may be used as a catalyst, but generally, it is preferred to mix the zeolite powder with an inorganic oxide binder such as alumina, silica, silica-alumina, or naturally occurring clays and form the mixture into tablets or extrudates. The final catalyst may contain from 1–99 wt. % SSZ-31 zeolite. Usually the zeolite content will range from 10–90 wt. %, and more typically from 60–80 wt. %. The preferred inorganic binder is alumina. The mixture may be formed into tablets or extrudates having the desired shape by methods well known in the art.

Examples of suitable aromatic hydrocarbon feedstocks which may be alkylated or transalkylated by the process of the invention include aromatic compounds such as benzene, toluene, and xylene. The preferred aromatic hydrocarbon is benzene. Mixtures of aromatic hydrocarbons may also be employed.

Suitable olefins for the alkylation of the aromatic hydrocarbon are those containing 2–20 carbon atoms, such as ethylene, propylene, butene-1, transbutene-2, and cis-butene-2, or mixtures thereof. The preferred olefin is propylene. These olefins may be present in admixture with the corresponding $C_2$ to $C_4$ paraffins, but it is preferable to remove any dienes, acetylenes, sulfur compounds or nitrogen compounds which may be present in the olefin feedstock stream to prevent rapid catalyst deactivation.

When transalkylation is desired, the transalkylating agent is a polyalkyl aromatic hydrocarbon containing two or more alkyl groups that each may have from two to about four carbon atoms. For example, suitable polyalkyl aromatic hydrocarbons include di-, tri-, and tetra-alkyl aromatic hydrocarbons, such as diethylbenzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

Reaction products which may be obtained include ethylbenzene from the reaction of benzene with either ethylene or polyethylbenzenes, cumene from the reaction of benzene with propylene or polyisopropylbenzenes, ethyltoluene from the reaction of toluene with ethylene or polyethyltoluenes, cymenes from the reaction of toluene with propylene or polyisopropyltoluenes, and secbutylbenzene from the reaction of benzene and n-butenes or polybutylbenzenes. The production of cumene from the alkylation of benzene with propylene or the transalkylation of benzene with di-isopropylbenzene is especially preferred.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 100°–600° F., preferably, 250°–450° F. The reaction pressure should be sufficient to maintain at least a partial liquid phase in order to retard catalyst fouling. This is typically 50–1000 psig depending on the feedstock and reaction temperature. Contact time may range from 10 seconds to 10 hours, but is usually from five minutes to an hour. The WHSV, in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 100°–600° F., but it is preferably about 250°–450° F. The reaction pressure should be sufficient to maintain at least a partial liquid phase, typically in the range of about 50–1000 psig, preferably 300–600 psig. The WHSV will range from about 0.1–10.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., platinum, include hydrogenation-dehydrogenation reactions, denitrogenation, and desulfurization reactions.

Some hydrocarbon conversions can be carried out on SSZ-31 zeolites utilizing the large pore shape-selective behavior. For example, the substituted SSZ-31 zeolite may be used in preparing cumene or other alkylbenzenes in processes utilizing propylene to alkylate aromatics. Such a process is described in our U.S. Ser. No. 134,410 (1987), using beta zeolite.

SSZ-31 can be used in hydrocarbon conversion reactions with active or inactive supports, with organic or inorganic binders, and with and without added metals. These reactions are well known to the art, as are the reaction conditions.

SSZ-31 can also be used as an adsorbent, as a filler in paper and paint, and as a water-softening agent in detergents.

The following examples illustrate the preparation of SSZ-31.

EXAMPLES

EXAMPLE 1

Preparation of N,N,N-Trimethyl-8-Ammonium Tricyclo[5.2.1.0] decane Hydroxide (Template A)

Five (5) grams of 8-ketotricyclo [5.2.1.0] decane (Aldrich Chemical Co.) was mixed with 2.63 gms of formic acid (88%) and 4.5 gms of dimethylformamide. The mixture was then heated in a pressure vessel for 16 hours at 190° C. Care should be taken to anticipate the increase in pressure the reaction experiences due to $CO_2$ evolution. The reaction was conveniently carried out in a Parr 4748 reactor with teflon liner. The workup consists of extracting N,N-dimethyl-8-amino tricyclo[5.2.1.0] decane from a basic (pH=12) aqueous solution with diethyl ether. The various extracts were dried with $Na_2SO_4$, the solvent removed and the product taken up in ethyl acetate. An excess of methyl iodide was added to a cooled solution which was then stirred at room temperature for several days. The crystals were collected and washed with diethyl ether to give N,N,N-trimethyl-8-ammonium tricyclo[5.2.1.0] decane iodide. The product has a melting point of 270°–272° C. and the elemental analyses and proton NMR are consistent with the expected structure. The vacuum-dried iodide salt was then ion-exchanged with ion-exchange resin AG 1×8 (in molar excess) to the hydroxide form. The exchange was performed over a column or more preferably by overnight stirring of the resin beads and the iodide salt in an aqueous solution designed to give about a 0.5 molar solution of the organic hydroxide. This is Template A (see Table 4).

EXAMPLE 2

1.5 Millimoles of the template from Example 1 were mixed with 0.035 gm of NaOH (solid) in 7.5 ml $H_2O$. 0.60 Gram of Cabosil M5 was stirred into the solution. The mixture was heated in a Parr 4745 reactor at 150° C. and without agitation for 20 days. The contents of the reactor were filtered, washed with distilled water, dried at 100° C. and analyzed by X-ray diffraction. The product was found to be the novel structure SSZ-31. The pattern is tabulated in Table 3 below.

TABLE 3

| $2\theta$ | d/n | $I/I_o$ |
|---|---|---|
| 4.26 | 20.7 | 5 |
| 6.10 | 14.49 | 6 |
| 7.36 | 12.01 | 30 |
| 8.18 | 10.81 | 11 |
| 10.72 | 8.25 | 1 |
| 12.03 | 7.36 | 1 |
| 14.33 | 6.18 | 1 |
| 14.71 | 6.02 | 1 |
| 15.91 | 5.57 | 2 |
| 17.46 | 5.08 | 7 |
| 18.44 | 4.811 | 9 |
| 20.30 | 4.374 | 15 |
| 21.12 | 4.206 | 69 |
| 21.38 | 4.156 | 9 |
| 22.24 | 3.997 | 100 |
| 22.68 | 3.921 | 7 |
| 24.73 | 3.600 | 23 |
| 25.19 | 3.535 | 11 |
| 25.70 | 3.466 | 5 |
| 26.70 | 3.339 | 9 |
| 27.20 | 3.278 | 5 |
| 27.70 | 3.220 | 5 |
| 28.18 | 3.167 | 2 |
| 28.77 | 3.103 | 4 |
| 29.00 | 3.079 | 3 |
| 29.50 | 3.028 | 2 |
| 29.82 | 2.996 | 5 |
| 30.56 | 2.925 | 2 |
| 30.90 | 2.894 | 11 |
| 32.16 | 2.783 | 5 |
| 32.76 | 2.734 | 6 |

EXAMPLE 3

The same reaction mixture of Example 2 was formed again. A Parr 4745 reactor was used but this time it was loaded onto a rotating (30 rpm) spit of a Blue M oven which was rotated at 30 RPM. The tumbling reactors were heated at 160° C. for 6 days. The analogous workup and analysis produced a crystalline SSZ-31.

EXAMPLE 4

2.25 Millimoles of template were mixed with 0.075 gm of NaOH (solid) and 12 ml of H$_2$O. 0.90 Gram of Cabosil were added and the reaction was run as in Example 3 except the Na/SiO$_2$ ratio had been increased. After 11 days of reaction, the product was mostly SSZ-31 but there was also some Kenyaiite and tridymite impurity.

EXAMPLE 5

The same experiment as in Example 4 was repeated with the following few changes. NaOH was replaced by 0.09 gms of KOH (solid) and the reaction was run at 150° C. and 0 RPM (no stirring) and required 22 days to crystallize. The product was SSZ-31 with a small amount of amorphous material.

EXAMPLE 6

Example 5 was repeated. However, the reaction was seeded with the product of Example 4. After 10 days at 160° C. but without stirring the product was SSZ-31 with a small impurity of Kenyaiite. This run demonstrates that crystallization, in the absence of stirring, can be made faster by the use of seed crystals.

EXAMPLE 7

(a) 5 Millimoles of the template of Example 1 and 0.06 gm NaOH(s) were mixed in 11.8 mL H$_2$O. 0.90 Gram Cabosil was stirred in to produce a homogeneous solution. 0.19 Gram of Nalco 1SJ 612 (26% SiO$_2$, 4% Al$_2$O$_3$) was added with stirring and several milligrams of seed crystals were also added. The sealed reaction was carried out at 160° C., 39 rpm, and over 10 days. The crystalline product was determined to be a very broadlined version of SSZ-31.

(b) When the same reaction was run without seed crystals and at 30 rpm, crystallization of SSZ-31 required 16 days.

EXAMPLE 8

The same experiment as Example 7 was repeated, except the source of aluminum was 0.05 gms Y zeolite (SK-40). Seeds of SSZ-31 were once again added. After 10 days at 160° C. and 30 rpm, the product had a broadlined version of SSZ-31 although not as broadened as in Example 7.

EXAMPLE 9

The crystalline products of Examples 2 and 4 were subjected to calcination as follows. The samples were heated in a muffle furnace from room temperature up to 540° C. at a steadily increasing rate over a 7-hour period. The samples were maintained at 540° C. for four more hours and then taken up to 600° C. for an additional four hours. A 50/50 mixture of air and nitrogen was passed over the zeolite at a rate of 20 standard cubic feet per minute during heating. The calcined product of Example 2 had the X-ray diffraction lines indicated in Table 4 below.

TABLE 4

| Calcined SSZ-31 | | |
| --- | --- | --- |
| 2θ | d/n | 100 × I/I$_o$ |
| 5.05 | 17.5 | 2 |
| 6.10 | 14.49 | 27 |
| 7.39 | 11.96 | 96 |
| 8.19 | 10.80 | 43 |

TABLE 4-continued

| Calcined SSZ-31 | | |
| --- | --- | --- |
| 2θ | d/n | 100 × I/I$_o$ |
| 10.35 | 8.55 | 1 |
| 10.81 | 8.18 | 6 |
| 12.20 | 7.25 | 2 |
| 14.45 | 6.13 | 14 |
| 14.84 | 5.97 | 9 |
| 16.00 | 5.54 | 1 |
| 17.54 | 5.06 | 5 |
| 18.46 | 4.806 | 6 |
| 20.37 | 4.360 | 13 |
| 21.10 | 4.210 | 64 |
| 21.53 | 4.127 | 4 |
| 22.40 | 3.969 | 100 |
| 23.78 | 3.742 | 1 |
| 24.85 | 3.583 | 14 |
| 25.20 | 3.534 | 4 |
| 26.20 | 3.401 | 14 |
| 26.80 | 3.326 | 6 |
| 27.70 | 3.220 | 2 |
| 28.20 | 3.164 | 1 |
| 28.95 | 3.084 | 3 |
| 29.18 | 3.060 | 3 |
| 29.83 | 2.995 | 3 |
| 30.00 | 2.979 | 3 |
| 31.00 | 2.885 | 7 |
| 32.32 | 2.770 | 3 |
| 32.86 | 2.726 | 3 |

EXAMPLE 10

Ion-exchange of the calcined materials from Example 9 was carried out using NH$_4$NO$_3$ to convert the zeolites from Na form to NH$_4$ and then eventually to the H form. Typically, the same mass of NH$_4$NO$_3$ as zeolite was slurried into H$_2$O at ratio of 50/1 H$_2$O to zeolite. The exchange solution was heated at 100° C. for two hours and then filtered. This process was repeated four times. Finally, after the last exchange, the zeolite was washed several times with H$_2$O and dried. A repeat calcination as in Example 9 was carried out but without the final treatment at 600° C. This produces the H form of the zeolites. The surface area for this material was 300 m$^2$/gm. The micro pore volume was 0.12 cc/gm as determined by the BET method with N$_2$ as absorbate.

EXAMPLE 11

The product of Example 7(b) was treated as in Examples 9 and 10. Next, the zeolite powder was pelletized in a Carver press at 1000 psi. The pellets were broken up and meshed to 24–40 size. 0.35 Gram of the hydrogen form was loaded into a ⅜-in. stainless steel tube with alumina packed on either side of the bed. The bed was heated in a Lindberg furnace and Helium (10 cc/min) was introduced into the reactor. The catalyst was heated to 700° F. Once temperature equilibration was achieved, a 50/50 w/w feed of n-hexane/3 methylpentane was introduced into the reactor at WHSV=0.68. The products were sampled on line by capillary G. C. At 10 minutes onstream, the conversion was 36% and indicated a large pore zeolite.

EXAMPLE 12

45 grams of 4-dimethylamino-2,2,6,6-tetramethyl piperidine (Aldrich) is dissolved in 1.5 L of ethyl acetate. The solution is chilled in an ice bath and 80 g of methyl iodide is added dropwise with stirring. The reaction is allowed to come to room temperature and is stirred for a few days. The reaction is filtered. The solids are washed with tetrahydrofuran and ether and then vacuum dried.

The crystalline salt is conveniently converted to the hydroxide form by stirring overnight in water with AG1-X8 hydroxide ion exchange resin to achieve a solution ranging from 0.25-1.5 molar. This is Template B (see Table 2).

EXAMPLE 13

4 grams of 3 Azabicyclo [3.2.2] nonane is stirred into 100 ml of methanol. 3 grams of potassium bicarbonate are added and the solution is chilled in an ice bath. Methyl iodide (10 gms) is added dropwise and the solution is stirred for 15-25 hours. The inorganic solids are filtered off and the methanol solution is stripped down. The residue is treated with $CHCl_3$ which extracts the product. The clear $CHCl_3$ phase is now stripped down and the solid product is recrystallized from a minimum of hot methanol. Subsequent filtration, washing and ion-exchange is similar to Example 12. This is Template C (see Table 2).

EXAMPLE 14

Template D (see Table 2) is prepared beginning with bicyclo[3.2.1] octa-2-one. The reaction sequence and molar ratios are the same as in Example 1.

EXAMPLE 15

Template E (see Table 2) is prepared from 6-Aza, 1,3,3 Trimethyl-bicyclo[3.2.1] octane. The procedure and molar ratios parallel Example 13.

EXAMPLE 16

3,5,5, Trimethyl azacycloheptane is alkylated with methyl iodide by the same procedure in Examples 13 and 15. The crystalline product is Template F (see Table 2).

EXAMPLE 17

2.25 millimoles of the hydroxide form of the template from Example 12 and 0.09 g NaOH (solid) in a total of 12 mL $H_2O$ are stirred until clear. 0.90 g of $NH_4+$ boron beta (aluminum free and described in U.S. Ser. No. 377,359) is added and the reaction is heated at 160° C. for six days and at 30 rpm. The product after filtration and washing, drying at 100° C., and XRD analysis is found to be SSZ-31 and some quartz impurity. No remaining beta zeolite is observed.

EXAMPLE 18

The same experiment as Example 17 is set up except the NaOH is reduced to 0.06 g. Seeds of all silica SSZ-31 are added (20 mg). Heating is carried out at 150° C. for six days, without stirring. The product is pure SSZ-31.

EXAMPLES 19-23

The following examples in Table 5 demonstrate the synthesis of SSZ-31 containing boron using templates B, C, D, E and F.

TABLE 5

Synthesis of Boron SSZ-31 Zeolite
(150° C., 4 days, 0 rpm)

| Ex # | Template | mMoles as OH | 1 N NaOH | $H_2O$* | $NH_4$ Boron Beta | XRD |
|---|---|---|---|---|---|---|
| 19 | B | 2.25 | 1.5 | 10.5 | 0.90 gms | SSZ-31 |
| 20 | C | 2.25 | 1.5 | 10.5 | 0.90 gms | SSZ-31 |
| 21 | D | 2.25 | 1.5 | 10.5 | 0.90 gms | SSZ-31 |
| 22 | E | 2.25 | 1.5 | 10.5 | 0.90 gms | SSZ-31 |
| 23 | F | 2.25 | 1.5 | 10.5 | 0.90 gms | SSZ-31 |

*Includes contribution from template solution and additional water added.

EXAMPLE 24

The X-ray diffraction data for the uncalcined product from Example 22 is presented in Table 6. The uncalcined product of Example 22 was calcined as follows. The sample was heated in a muffle furnace from room temperature up to 540° C. at a steadily increasing rate over a 7-hour period. The sample was maintained at 540° C. for four more hours and then taken up to 600° C. for an additional four hours. Nitrogen was passed over the zeolite at a rate of 20 standard cfm during heating. The calcined product had the X-ray diffraction lines indicated in Table 7 below.

TABLE 6

X-Ray Diffraction Pattern for Uncalcined Product

| $2\theta$ | d/n | Intensity |
|---|---|---|
| 6.08 | 14.54 | 17 |
| 7.35 | 12.03 | 17 |
| 8.00 | 11.05 | 12 (Broad) |
| 16.00 | 5.54 | 2 (Broad) |
| 17.40 | 5.10 | 5 (Broad) |
| 18.48 | 4.80 | 19 |
| 20.35 | 4.36 | 16 (Broad) |
| 21.11 | 4.21 | 180 |
| 22.24 | 4.00 | 100 |
| 22.62 | 3.93 | 10 |
| 24.71 | 3.60 | 38 |
| 25.60 | 3.48 | 3 (Broad) |
| 26.70 | 3.34 | 3 (Broad) |
| 30.88 | 2.90 | 12 |

TABLE 7

X-Ray Diffraction Pattern for Calcined Product

| $2\theta$ | d/n | Intensity |
|---|---|---|
| 6.13 | 14.42 | 65 |
| 7.43 | 11.90 | 52 |
| 8.10 | 10.92 | 33 |
| 10.80 | 8.19 | 4 (Broad) |
| 12.35 | 7.17 | 2 (Broad) |
| 14.48 | 6.12 | 5 |
| 14.85 | 5.97 | 4 |
| 17.55 | 5.05 | 3 (Broad) |
| 18.07 | 4.91 | 12 |
| 20.45 | 4.34 | 10 |
| 21.17 | 4.20 | 150 |
| 21.57 | 4.12 | 10 |
| 22.43 | 3.96 | 75 |
| 24.88 | 3.58 | 27 |
| 26.70 | 3.34 | 3 (Broad) |
| 31.07 | 2.88 | 8 |

EXAMPLE 25

Ion exchange of the calcined material from Example 17 was carried out using $NH_4NO_3$ to convert the zeolites from Na form to $NH_4$. Typically the same mass of $NH_4NO_3$ as zeolite was slurried into $H_2O$ at ratio of 50:1 $H_2O$:zeolite. The exchange solution was heated at 100° C. for two hours and then filtered. This process was repeated two times. Finally, after the last exchange, the zeolite was washed several times with $H_2O$ and dried.

EXAMPLE 26

Constraint Index Determination 0.50 g of the hydrogen form of the zeolite of Example 17 (after treatment according to Examples 24 and 25) was packed into a ⅜-inch stainless steel tube with alundum on both sides of the zeolite bed. A lindburg furnace was used to heat the reactor tube. Helium was introduced into the reactor tube at 10 cc/minute and atmospheric pressure. The reactor was taken to 250° F. for 40 minutes and then raised to 800° F. Once temperature equilibration was achieved, a 50/50, w/w feed of n-hexane and 3-methylpentane was introduced into the reactor at a rate of 0.62 cc/hour. Feed delivery was made via syringe pump. Direct sampling onto a gas chromatograph was begun after 10 minutes of feed introduction. Constraint Index values were calculated from gas chromatographic data using methods known in the art.

| Synthesis Example No. | C.I. | Conversion at 10 Min. | Temp., °F. |
|---|---|---|---|
| 17 | — | 0 | 800 |

EXAMPLE 27

The product of Example 17 after treatment as in Examples 24 and 25 is refluxed overnight with Al(-$NO_3$)$_3$·9$H_2O$ with the latter being the same mass as the zeolite and using the same dilution as in the ion exchange of Example 25. The product is filtered, washed, and calcined to 540° C. After pelletizing the zeolite powder and retaining the 20–40 mesh fraction, the catalyst is tested as in Example 26. Data for the reaction is given in Table 8.

TABLE 8

Constraint Index Determination For Metal-Treated (B)SSZ-31

| Synthesis Example No. | Metal Salt | C.I. | Conversion, % (10 Min.) | Temp., °F. |
|---|---|---|---|---|
| 17 | None | — | 0 | 800 |
| 17 | Al(NO$_3$)$_3$ | 0.89 | 34 | 700 |

EXAMPLE 28

The all-silica version of SSZ-31 was evaluated as a reforming catalyst. The zeolite powder was impregnated with Pt(NH$_3$)$_4$·2NO$_3$ to give 0.7 wt. % Pt. The material was calcined up to 600° F. in air and maintained at this temperature for three hours. The powder was pelletized on a Carver press at 1000 psi and broken and meshed to 24–40.

The catalyst was evaluated at 950° F. in hydrogen under the following conditions:

| psig = | 200 |
|---|---|
| H$_2$/HC = | 6.4 |
| WHSV = | 6 |
| Temp. = | 950° F. |

The feed was an iC$_7$ mixture (Philips Petroleum Company):

| | Feed | Product 1.5 Hours Onstream, % |
|---|---|---|
| Conversion, % | | 36 |
| Toluene | 0.52 | 7.10 |
| C$_5$-C$_8$ Octane | 63.7 | 69.7 |

EXAMPLE 29

The product of Example 7(a) was treated as in Examples 9 and 10. This catalyst now contained acidity due to aluminum incorporation. Two back ion-exchanges with KNO$_3$ were performed and the catalyst was calcined to 1000° F. Next, a reforming catalyst was prepared as in Example 28. The catalyst was evaluated under the following conditions:

| psig = | 200 |
|---|---|
| H$_2$/HC = | 6.4 |
| WHSV = | 6 |
| Temp. = | 800° F. |

The feed has an iC$_7$ mixture (Philips Petroleum Company). The data for the run is given in Table 9. After 23 hours on stream, the temperature was raised to 900° F. and this data also appears in the Table. By comparison with Example 28, the incorporation of aluminum into the zeolite gives a more active reforming catalyst.

TABLE 9

| Time | 0.5 hrs. | 1 hr (after 23 hrs. at 800° F.) |
|---|---|---|
| Temp. | 800° F. | 900° F. |
| Conversion | 19.4% | 35.6% |
| Aromatization Select. | 43.7% | 55.6% |
| Toluene in Product | 7.82% | 18.93% |
| % Toluene in C$_5$+ aromatics | 92% | 96% |
| C$_5$–C$_8$ RON | 67.2 | 72.7 |

EXAMPLE 30

The product of Example 7(a) was treated as in Examples 9 and 10. Next, the catalyst was dried at 600° F., cooled in a closed system and then vacuum impregnated with an aqueous solution of Pd (NH$_3$)$_4$ 2 NO$_3$ to give 0.5 wt. % loading of palladium. The catalyst was then calcined slowly up to 900° F. in air and held there for three hours. Table 10 gives run conditions and product data for the hydrocracking of hexadecane. The catalyst is quite stable at the temperatures given.

TABLE 10

| Temp. | 535° F. | 560° F. |
|---|---|---|
| WHSV | 1.55 | 1.55 |
| PSIG | 1200 | 1200 |
| Conversion | 94.2 | 99.8 |
| Isom. select. | 83.3 | 17.2 |
| Crack. select. | 16.7 | 82.9 |
| C$_5$+/C$_4$ | 18 | 13.3 |
| C$_5$+ C$_6$/C$_5$+ | 13.2 | 17.9 |

The data shows that the catalyst has good isomerization selectivity and that the liquid yield is high compared with the gas make.

EXAMPLE 31

The acid form of SSZ-31 was prepared as in Example 27 and tested for the conversion of methanol to liquid products. 0.5 gm of catalyst was loaded into a ⅜-inch stainless steel reactor tube which was heated in a Lindberg furnace to 1000° F. The temperature was reduced to 700° F. in a stream of helium at 20 cc/min. Methanol was introduced into the reactor at a rate of 1.15 cc/hr. The conversion at 5 minutes was 100% and dropped over several hours. The product distribution is given in Table 11 below.

TABLE 11

Conversion of Methanol over SSZ-31 Zeolite (at 5 min.)

| Product | Wt. % |
|---|---|
| Methane | 1.4 |
| Ethylene | 3.7 |
| Ethane | 0.2 |
| Propylene | 3.5 |
| Propane | 3.5 |
| Isobutane | 8.3 |
| Methanol | <0.1 |
| Dimethyl ether | 0.0 |
| 1-Butene | 0.7 |
| n-Butane | 1.5 |
| 1-Pentene | 2.9 |
| 2-Methylpentane | 0.7 |
| Toluene | 0.4 |
| p-Xylene, m-Xylene | 0.5 |
| o-Xylene | <0.1 |
| 1,3,5-Trimethylbenzene | 0.9 |
| 1,2,4-Trimethylbenzene | 2.5% |
| 1,2,3-Trimethylbenzene | 0.5% |
| 1,2,4,5-Tetramethylbenzene, 1,2,3,5-Tetramethylbenzene | 18.6% |
| 1,2,3,4-Tetramethylbenzene | 3.1% |
| Pentamethylbenzene | 31.9 |
| Hexamethylbenzene | 5.3 |
| Identified Peaks | 86.5% |
| Unidentified Peaks (Greater than $C_6$ or $C_7$) | 13.5% |

EXAMPLE 32

The boron version of SSZ-31 from Example 19 was evaluated as a reforming catalyst. The zeolite powder was impregnated with $Pt(NH_3)_4 \cdot 2NO_3$ to give 0.7 wt. % Pt. The material was calcined up to 600° F. in air and maintained at this temperature for three hours. The powder was pelletized on a Carver press at 1000 psi and broken and meshed to 24-40.

The catalyst was evaluated at 800° F. in hydrogen under the following conditions:

| | Run 1 | Run 2 |
|---|---|---|
| psig | 200 | 50 |
| $H_2/HC$ | 6.4 | 6.4 |
| WHSV | 6 | 6 |
| Temp. | 800° F. | 800° F. |
| Time | 23 hours | 24 hours |

The feed was an $iC_7$ mixture (Philips Petroleum Company).

| | Feed | Run 1 Product % | Run 2 Product % |
|---|---|---|---|
| Conversion, % | 0 | 68.1 | 69.7 |
| Aromatization Select. | 0 | 39.4 | 54.7 |
| Toluene | 0.68 | 24.55 | 36.02 |
| $C_5-C_8$ RON | 63.9 | 82.8 | 87.6 |

What is claimed is:

1. A process for converting hydrocarbons comprising contacting a hydrocarbonaceous feed at hydrocarbon converting conditions with a calcined zeolite having a mole ratio of an oxide selected from silicon oxide, germanium oxide and mixtures thereof to an oxide selected from aluminum oxide, gallium oxide, iron oxide, and mixtures thereof greater than about 50:1, and having the X-ray diffraction lines of the as-synthesized zeolite in Table 1.

2. A process in accordance with claim 1 which is a hydrocracking process comprising contacting the hydrocarbon feedstock under hydrocracking conditions with a calcined zeolite having a mole ratio of an oxide selected from silicon oxide, germanium oxide and mixtures thereof to an oxide selected from aluminum oxide, gallium oxide, iron oxide, and mixtures thereof greater than about 50:1, and having the X-ray diffraction lines of the as-synthesized zeolite in Table 1.

3. A process in accordance with claim 1 wherein the process is a hydrodewaxing process comprising contacting the hydrocarbon feedstock under hydrodewaxing conditions with a calcined zeolite having a mole ratio of an oxide selected from silicon oxide, germanium oxide and mixtures thereof to an oxide selected from aluminum oxide, gallium oxide, iron oxide, and mixtures thereof greater than about 50:1, and having the X-ray diffraction lines of the as-synthesized zeolite in Table 1.

4. A process in accordance with claim 1 wherein the process is a catalytic cracking process comprising the step of contacting the hydrocarbon feedstock in a reaction zone under catalytic cracking conditions in the absence of added hydrogen with a catalyst comprising a calcined zeolite having a mole ratio of an oxide selected from silicon oxide, germanium oxide and mixtures thereof to an oxide selected from aluminum oxide, gallium oxide, iron oxide, and mixtures thereof greater than about 50:1, and having the X-ray diffraction lines of the as-synthesized zeolite in Table 1.

5. A process in accordance with claim 1 wherein the process is a catalytic cracking process comprising the step of contacting the hydrocarbon feedstock in a reaction zone under catalytic cracking conditions in the absence of added hydrogen with a catalyst composition comprising a calcined zeolite having a mole ratio of an oxide selected from silicon oxide, germanium oxide and mixtures thereof to an oxide selected from aluminum oxide, gallium oxide, iron oxide, and mixtures thereof greater than about 50:1, and having the X-ray diffraction lines of the as-synthesized zeolite in Table 1 in and a large pore size crystalline aluminosilicate cracking component.

6. A process as defined in claim 5 wherein the crystalline aluminosilicate cracking component has a pore size greater than 7.0 angstroms.

7. A process in accordance with claim 5 wherein the catalyst composition comprises a physical mixture of the two components.

8. A process in accordance with claim 5 wherein one of the components is incorporated in an inorganic oxide selected from the group consisting of silica, alumina, amorphous silica-alumina, silica-magnesia, silica zirconia, alumina-boria, alumina-titanate, a synthetic clay such as synthetic mica-montmorillonite, natural clays such as kaolin, halloysite, montmorillonite, attapulgite, sepiolite, saponite, acid activated clays, pillared clays, cross-linked clays, and mixtures thereof.

9. A process in accordance with claim 5 wherein the two catalyst components are incorporated in an inorganic matrix comprised of an inorganic oxide selecting from the group consisting of silica, alumina, amorphous silica-alumina, silica-magnesia, silica zirconia, alumina-boria, alumina-titanate, a synthetic clay such as synthetic mica-montmorillonite, natural clays such as kaolin, halloysite, montmorillonite, attapulgite, sepiolite, saponite, acid activated clays, pillared clays, cross-linked clays, and mixtures thereof.

10. A process in accordance with claim 1 wherein the process is an isomerizing process for isomerizing $C_4$ to $C_7$ hydrocarbons, comprising contacting a catalyst, comprising at least one Group VIII metal and a calcined zeolite having a mole ratio of an oxide selected from silicon oxide, germanium oxide and mixtures thereof to an oxide selected from aluminum oxide, gallium oxide, iron oxide, and mixtures thereof greater than about 50:1, and having the X-ray diffraction lines of the as-synthesized zeolite in Table 1, with a feed having normal and slightly branched $C_4$ to $C_7$ hydrocarbons under isomerization conditions.

11. A process in accordance with claim 10 wherein the catalyst has been calcined in a steam/air mixture at an elevated temperature after impregnation of the Group VIII metal.

12. A process in accordance with claim 10 wherein Group VIII metal is platinum.

13. A process in accordance with claim 1 wherein the process is an oligomerization process comprising contacting an olefin feed under oligomerization conditions with a calcined zeolite having a mole ratio of an oxide selected from silicon oxide, germanium oxide and mixtures thereof to an oxide selected from aluminum oxide, gallium oxide, iron oxide, and mixtures thereof greater than about 50:1, and having the X-ray diffraction lines of the as-synthesized zeolite in Table 1.

14. A process in accordance with claim 1 wherein the process is a catalytic reforming process comprising contacting a hydrocarbonaceous feedstream under catalytic reforming conditions with a calcined zeolite having a mole ratio of an oxide selected from silicon oxide, germanium oxide and mixtures thereof to an oxide selected from aluminum oxide, gallium oxide, iron oxide, and mixtures thereof greater than about 50:1, and having the X-ray diffraction lines of the as-synthesized zeolite in Table 1.

15. A process for preparing a high octane product having an increased aromatics content comprising:
(a) contacting a hydrocarbonaceous feed, which comprises normal and slightly branched hydrocarbons having a boiling range above about 40° C. and less than about 200° C. under aromatic conversion conditions with a calcined zeolite having a mole ratio of an oxide selected from silicon oxide, germanium oxide and mixtures thereof to an oxide selected from aluminum oxide, gallium oxide, iron oxide, and mixtures thereof greater than about 50:1, and having the X-ray diffraction lines of the as-synthesized zeolite in Table 1, wherein said zeolite is substantially free of acidity; and
(b) recovering an effluent having a higher octane than said hydrocarbonaceous feed.

16. A process in accordance with claim 10 wherein the zeolite contains a Group VIII metal component.

17. A process for alkylating an aromatic hydrocarbon which comprises contacting under alkylating conditions at least a mole excess of an aromatic hydrocarbon with a $C_2$ to $C_{20}$ olefin under at least partial liquid phase conditions and in the presence of a calcined zeolite having a mole ratio of an oxide selected from silicon oxide, germanium oxide and mixtures thereof to an oxide selected from aluminum oxide, gallium oxide, iron oxide, and mixtures thereof greater than about 50:1, and having the X-ray diffraction lines of the as-synthesized zeolite in Table 1.

18. A process in accordance with claim 17 wherein the aromatic hydrocarbon and olefin are present in a molar ratio of about 4:1 to 20:1, respectively.

19. A process in accordance with claim 17 wherein the aromatic hydrocarbon is a member selected from the group consisting of benzene, toluene and xylene, or mixtures thereof.

20. A process for transalkylating an aromatic hydrocarbon which comprises contacting under transalkylating conditions an aromatic hydrocarbon with a polyalkyl aromatic hydrocarbon under at least partial liquid phase conditions and in the presence of a calcined zeolite having a mole ratio of an oxide selected from silicon oxide, germanium oxide and mixtures thereof to an oxide selected from aluminum oxide, gallium oxide, iron oxide, and mixtures thereof greater than about 50:1, and having the X-ray diffraction lines of the as-synthesized zeolite in Table 1.

21. A process in accordance with claim 20 wherein aromatic hydrocarbon and said polyalkyl aromatic hydrocarbon are present in a molar ratio of about 1:1 to about 25:1, respectively.

22. A process in accordance with claim 20 wherein the aromatic hydrocarbon is a member selected from the group consisting of benzene, toluene and xylene, or mixtures thereof.

23. A process in accordance with claim 20 wherein the polyalkyl aromatic hydrocarbon is dialkylbenzene.

24. A process for preparing a product having an increased aromatic content comprising:
(a) contacting a hydrocarbonaceous feed, which comprises normal and slightly branched hydrocarbons having a boiling range above about 40° C. and less than about 200° C. under aromatic conversion conditions with a calcined zeolite having a mole ratio of an oxide selected from silicon oxide, germanium oxide and mixtures thereof to an oxide selected from aluminum oxide, gallium oxide, iron oxide, and mixtures thereof greater than about 50:1, and having the X-ray diffraction lines of the as-synthesized zeolite in Table 1, wherein said zeolite is substantially free of acidity; and
(b) recovering an aromatic-containing effluent.

25. A process for the catalytic conversion of lower aliphatic alcohols having 1 to 8 carbon atoms to form gasoline boiling range hydrocarbons which comprises contacting the alcohols under converting conditions with a calcined zeolite having a mole ratio of an oxide selected from silicon oxide, germanium oxide and mixtures thereof to an oxide selected from aluminum oxide, gallium oxide, iron oxide, and mixtures thereof greater than about 50:1, and having the X-ray diffraction lines of the as-synthesized zeolite in Table 1.

26. The process of claim 25 wherein the alcohol is methanol.

27. A process for converting a $C_2$–$C_6$ olefin or paraffin feedstream to aromatic compounds comprising contacting the feed material under aromatic conversion conditions with a calcined zeolite having a mole ratio of an oxide selected from silicon oxide, germanium oxide and mixtures thereof to an oxide selected from aluminum oxide, gallium oxide, iron oxide, and mixtures thereof greater than about 50:1, and having the X-ray diffraction lines of the as-synthesized zeolite in Table 1.

* * * * *